(12) United States Patent
Nilsson

(10) Patent No.: US 9,675,746 B2
(45) Date of Patent: Jun. 13, 2017

(54) METHOD AND PRODUCT FOR BLOOD TREATMENT AND PURIFICATION

(75) Inventor: Kurt G. I. Nilsson, Lund (SE)

(73) Assignee: GLYCOREX AB, Lund (SE)

( * ) Notice: Subject to any disclaimer, the term of this patent is extended or adjusted under 35 U.S.C. 154(b) by 0 days.

(21) Appl. No.: 13/501,640

(22) PCT Filed: Oct. 18, 2010

(86) PCT No.: PCT/SE2010/051124
§ 371 (c)(1),
(2), (4) Date: May 22, 2012

(87) PCT Pub. No.: WO2011/046504
PCT Pub. Date: Apr. 21, 2011

(65) Prior Publication Data
US 2012/0230969 A1    Sep. 13, 2012

(30) Foreign Application Priority Data
Oct. 18, 2009   (SE) ........................................ 0901341

(51) Int. Cl.
*A01N 63/00* (2006.01)
*C12N 5/00* (2006.01)
(Continued)

(52) U.S. Cl.
CPC ........ *A61M 1/3472* (2013.01); *A61M 1/3486* (2014.02)

(58) Field of Classification Search
None
See application file for complete search history.

(56) References Cited

U.S. PATENT DOCUMENTS 4,352,884 A * 10/1982 Nakashima et al. .......... 435/180
4,678,566 A    7/1987 Watanabe et al.
(Continued)

FOREIGN PATENT DOCUMENTS

| | | |
|---|---|---|
| EP | 1 219 639 | 9/2000 |
| WO | 2006/094467 | 9/2006 |
| WO | 2009/086203 | 7/2009 |

OTHER PUBLICATIONS

Tullis et al., Blood Purif, 21:58-63 (2003).*
International Search Report for PCT/SE2010/051124 mailed Jan. 28, 2011.

*Primary Examiner* — Thomas J Visone
(74) *Attorney, Agent, or Firm* — Smith, Gambrell & Russell, LLP

(57) ABSTRACT

Extracorporeal blood treatment is performed daily on a large number of patients by use of for example a dialysis filter, plasma filter or a centrifuge. The purpose of the treatment is to separate minor components and molecules in a liquid or in the blood from larger ones, for example in connection with different disease conditions or with a view to extracting blood plasma, target substances such as blood components or molecules from for example blood donors. According to the present invention two separation steps are used together with a solution or a suspension containing at least one component, which specifically may bind to the component or the blood component to be specifically reduced, or to be refined/extracted during the treatment or during the blood treatment.

24 Claims, 1 Drawing Sheet

(51) Int. Cl.
*C12N 5/02* (2006.01)
*A61M 1/34* (2006.01)

(56) References Cited

U.S. PATENT DOCUMENTS

| | | | |
|---|---|---|---|
| 4,702,841 A * | 10/1987 | Sengbusch | 210/638 |
| 4,770,774 A * | 9/1988 | Ida et al. | 210/259 |
| 4,787,974 A * | 11/1988 | Ambrus et al. | 210/321.8 |
| 4,946,677 A * | 8/1990 | Dorner et al. | 424/260.1 |
| 5,022,988 A * | 6/1991 | Okarma et al. | 210/321.84 |
| 5,536,412 A * | 7/1996 | Ash | 210/645 |
| 5,782,792 A * | 7/1998 | Jones et al. | 604/6.05 |
| 5,919,369 A * | 7/1999 | Ash | 210/645 |
| 6,080,404 A * | 6/2000 | Branham et al. | 424/140.1 |
| 6,221,614 B1 | 4/2001 | Prusiner et al. | 435/7.1 |
| 6,332,985 B1 * | 12/2001 | Sherman et al. | 210/638 |
| 6,528,057 B1 * | 3/2003 | Ambrus et al. | 424/140.1 |
| 6,686,457 B1 * | 2/2004 | Nilsson | 536/4.1 |
| 6,746,607 B1 | 6/2004 | Vijayalakshmi et al. | |
| 2001/0021525 A1 * | 9/2001 | Hirai et al. | 435/283.1 |
| 2002/0045157 A1 * | 4/2002 | Hirai et al. | 435/2 |
| 2002/0146814 A1 * | 10/2002 | Nilsson | 435/287.1 |
| 2003/0012941 A1 * | 1/2003 | Fujita et al. | 428/304.4 |
| 2003/0013862 A1 * | 1/2003 | Seeberger et al. | 536/18.7 |
| 2004/0004041 A1 * | 1/2004 | Hiiro et al. | 210/660 |
| 2004/0022784 A1 * | 2/2004 | Nilsson | 424/140.1 |
| 2004/0137542 A1 * | 7/2004 | Petyaev | 435/7.32 |
| 2004/0226874 A1 * | 11/2004 | Nanko et al. | 210/266 |
| 2004/0242857 A1 * | 12/2004 | Nilsson | 536/3 |
| 2005/0006296 A1 * | 1/2005 | Sullivan et al. | 210/321.6 |
| 2005/0009001 A1 * | 1/2005 | Seidel et al. | 435/2 |
| 2005/0238641 A1 * | 10/2005 | Burton et al. | 424/140.1 |
| 2006/0017142 A1 * | 1/2006 | Jang et al. | 257/672 |
| 2006/0093588 A1 * | 5/2006 | Nilsson | 424/93.7 |
| 2007/0276351 A1 * | 11/2007 | Nilsson | 604/406 |
| 2008/0234621 A1 * | 9/2008 | Bellotti et al. | 604/5.03 |
| 2010/0152425 A1 * | 6/2010 | Nilsson | 530/387.1 |
| 2011/0009796 A1 | 1/2011 | Tullis et al. | |

\* cited by examiner

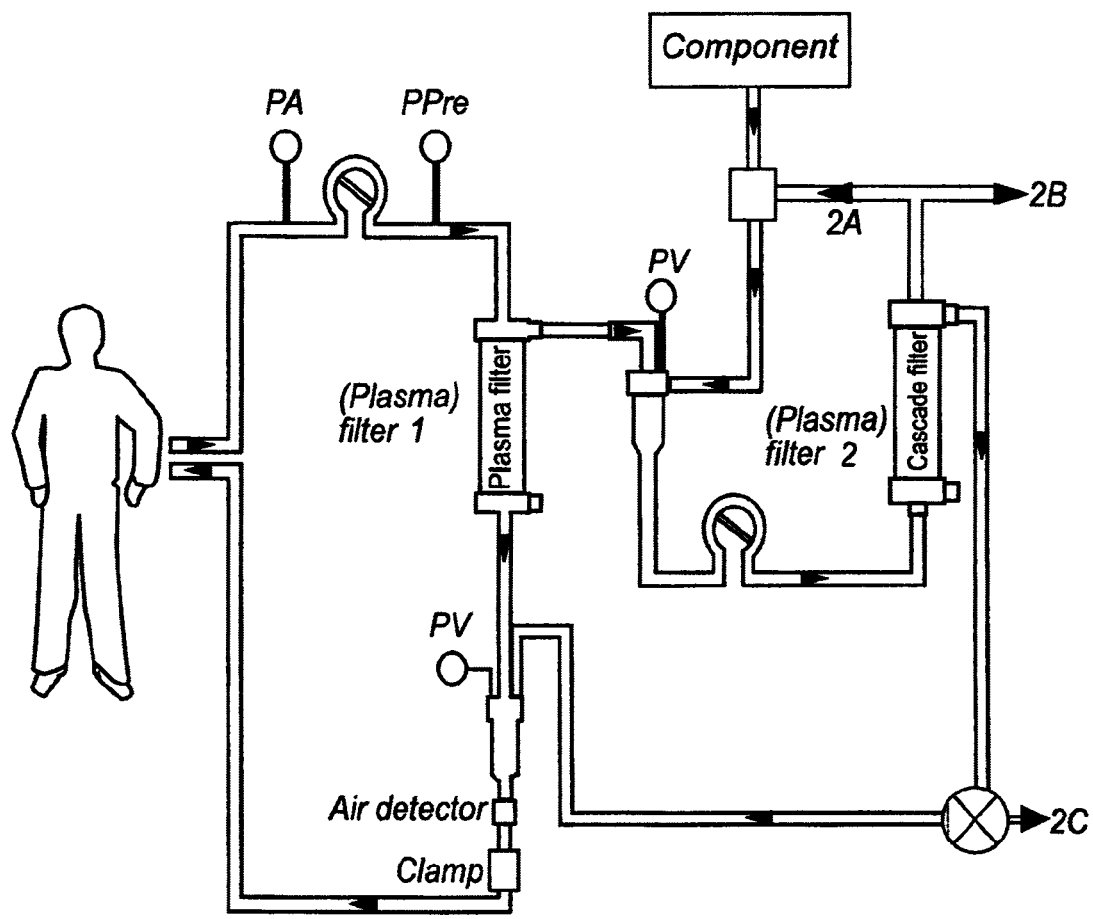

METHOD AND PRODUCT FOR BLOOD TREATMENT AND PURIFICATION

Extracorporeal blood treatment is performed daily on a large number of patients, e.g. by use of a dialysis filter, a plasma filter or a centrifuge.

The purpose of the treatment is to separate smaller components and molecules from larger ones in the blood in connection with different disease conditions or to extract blood plasma, target substances such as blood components or molecules from blood donors.

In dialysis, plasma exchange (therapeutic plasma exchange, TPE) or double filter treatments (DFPP, filters having different pore size for each treatment are used.

In dialysis filters allowing passage of relatively small molecules (normally less than 67,000 in molecular weight) are used. In plasma exchange blood filters (unless a centrifugation method is used) having a larger pore size allowing passage of all plasma components in the blood except red blood cells and white blood cells are used. In the case of DFPP two filters are used, one "coarse" filter of the same type that is used in plasma exchange and a filter having a smaller pore size separating plasma components depending on size.

Thus, all of the above-mentioned methods make possible a separation based on molecular weight and size of the different blood components. However, these methods do not give any biospecific separation, i.e. based on the biological specificity of each blood component.

Therefore, an approach called immunospecific blood treatment (IA) has been introduced, wherein a biospecific column is used during the treatment.

IA makes possible a specific treatment, i.e. specific elimination or reduction of a target substance during the treatment, e.g. immunoglobulin G, from other proteins in the blood, but also separation from proteins having a similar molecular weight/size as immunoglobulin G.

Columns containing protein A are examples of these. These columns contain covalently bound protein A. Other examples are immunoglobulin-based columns for specific elimination of immunoglobulins or for separation of other proteins from plasma. Other examples are columns having a covalently bound blood group antigen with a view to specifically binding that part of antibodies in the blood which is specific for the blood group determinants A and B, respectively, while other antibodies and other blood components pass through the column.

In IA a plasma filter (like in PE) or a centrifuge is normally used, which continuously separates the plasma from the blood cells, and the plasma is transported through a tube to a column in which the target protein/substance is bound and thereby is specifically separated from other plasma components. Blood plasma which has passed through the column is transported back to the patient.

Thus, the IA treatment takes place in a system having two circuits, one blood conduit leading away from and back to the patient with separated blood cells after the plasma filter and a plasma conduit containing the IA column after the plasma filter. The two conduits are connected before the return to the patient, and the treatment is continuous.

The problem with the above-mentioned IA column treatment is that several columns having different geometry and methods of production have to be designed for the different specific treatments and that several types of columns, e.g. protein A and immunoglobulin columns, become saturated and have to be regenerated during the treatment. The flow rate through the column is often a limiting factor and prolongs the treatment time. The size of the patients and different degrees of abnormality to be treated make treatment with a column troublesome in view of the adaption of the treatment to the patient.

A problem with the physical size-dependent PE and DFPP treatments is that they are not specific and that they, in addition to the target substance/target substances, also eliminate a large number of other important components in the blood. This creates undesired side effects, e.g. not only antibodies are eliminated, but also a large quantity of other important blood components in DFPP. Replacement liquids containing e.g. albumin, IVIG injections for the replacement of immunoglobulins, and coagulation factors pass through the column and have to be replaced.

The present invention discloses a product and a method in which these drawbacks are avoided or minimized.

In the present invention two separation steps are used together with a solution or a suspension containing at least one component which has the ability to specifically bind to the component or blood component to be specifically reduced or to be refined/extracted during the treatment or during the blood treatment.

In one example of an embodiment of the present invention the two separation steps are performed by use of two coarse filters. The term coarse filter is here intended to mean a filter of the same or similar type which normally is used in PE and having pores which allow the passage of plasma but not of red and white blood cells. In an another embodiment according to the present invention one coarse filter and one filter having a smaller pore size than the coarse filter are used.

The component (called the Component below) used according to the present invention to specifically bind to the target component/substance that is to be reduced in the blood is soluble or forms a suspension in the buffer used during the treatment.

According to the present invention the treatment is performed in two connected steps. In step 1 blood cells are separated, for example, from plasma with a coarse filter or a centrifuge, and in step 2 the separated blood plasma is transported onwards and is mixed with the Component binding the target components/substance, and in the subsequent blood filter the plasma is separated from the Component having a bound target substance (antibody, protein, virus, bacterium, bacteria component, cell). The plasma is then returned to the patient, like in IA and DFPP.

The separation of the Component and the Component having a target substance/component bound thereto takes place because these cannot pass through the filter in step 2, in contrast to the plasma. The treated plasma having a reduced content of the target substance/component to be reduced is recirculated to the patient via the blood conduit.

The treatment may be performed continuously or with interruptions with a view to washing the second filter from the Component having a target substance/component bound thereto. The solution involving the Component may continuously be transported to a "waste bag" during the treatment or be continuously returned to the second filter. This, as well as the chosen pore size, the apparatus (there is a large number of commercially available filters, as well as different centrifuges and machines for plasma treatments) are determined by the person skilled in the art, as well as the flow rates, the amount of the Component, the treatment period, the temperature and the pressure in the different blood and plasma conduits during the treatment, as well as other parameters. Thus, this does not limit the scope of the present invention.

In this way several of the advantages associated with IA and DFPP are obtained, and at the same time several of the disadvantages encountered when using the IA and DFPP method, respectively, are avoided.

The Component according to the present invention consists of at least two partial components, i.e. one matrix and one ligand. The matrix may for example be built up by dextran, polyehtyleneglycol or another substance or polymer which is soluble in the aqueous buffer (e.g. PA buffer or saline buffer) which is used with a view to dissolving the Component. The Component contains at least one covalently bound ligand, e.g. biotin or another biomolecule having affinity to another biomolecule, virus, bacterium, bacterium component or cell, such as a peptide, protein, immunoglobuline, enzyme, saccharide (mono-, di-, tri-, tetra-, penta-, hexasaccharide or higher saccharide).

The matrix may also consist of a non-soluble polymer, e.g. consisting of a plastic or a polymer or a polysaccharide. There are several examples thereof having several configurations and these do not limit the scope of invention. As non-limiting examples cross-linked agarose in the form of porous microparticles, also commercially available as e.g. Sepharose, could be mentioned. Several variants of this exist and do not limit the scope of invention. The amount, the pore size and the size of the matrix, e.g. in the form of microspheres or microparticles, do not limit the scope of invention. A typical size of the matrix is from 1 micrometer up to 300 micrometers in particle size and any average size of the particles within this interval.

The molecular size of the dextran, the polyethylene glycol and any other soluble substance may be chosen by the person skilled in the art. Typical sizes are any size within the interval from 100,000 to 1 million Daltons. The size of the matrix is chosen, inter alia, with regard to the capacity and the fact that the second filter used according to the present invention should not allow passage of the matrix, wherein the treated plasma returned to the patient does not contain the matrix and not the matrix having the target substance/component bound thereto.

The ligand is covalently bound to the matrix. This can take place by use of one or more methods chosen by a person skilled in the art from a large number of different methods. This does not limit the scope of the present invention. Non-limiting methods, e.g. the NHS, EDC, epoxy, CNBr, tosyl, tresyl method, and a di-, tri-, tetra- etc, functional cross-linker etc, may be used. Examples of bonds between the ligand and the matrix are for example an amide bond between the ligand and the matrix, isourea, C—S binding, C—N binding, etc. The ligand may be provided with a so-called spacer with a view to distancing the matrix from the ligand, and the choise of this does not limit the scope of the present invention.

The Component may also contain covalently bound biotin which may be used with a view to binding avidin or streptavidin, to which the desired ligand (protein A, another protein, antibody, saccharide) thereafter have been covalently bound, e.g. with EDC, NHS, or a cross-linker. In this way the biotin matrix may be used for several different target substances/components that are to be reduced in blood.

A FIGURE representing the treatment according to the invention is schematically shown as a non-limiting example in FIG. 1.

Several variants of the configuration above may be used according to the present invention and do not limit the scope thereof. The plasma filter may be replaced by a centrifuge, as well as the filter in step 2 above. The P represents pressure gauges. The Component with the ligand may be added continuously or at the beginning of the treatment. The Component with the ligand may be returned to the plasma conduit after passing through filter 2 (according to 2A above) or be transported to a so-called waste bag (according to 2B above), or be collected after the treatment above with a view to refining the target substance, in this case the substance to be extracted. In the latter case the target substance may be eluted from the Component, e.g. by a change of the pH, wherein for example antibodies and/or proteins are eluted from the Component with a glycine buffer as a non-limiting example, e.g. 0.1 M, pH 2.2 or another desired buffer, concentration, and pH chosen by the person skilled in the art for the specific target substance.

The patient in the scheme above may be replaced by blood donor plasma or another liquid containing the substance to be refined or eliminated from the liquid. In this case the blood donor plasma or said another liquid is treated according to step 1 and step 2 above. The plasma or the liquid may be collected with a reduced amount of the target substance. Alternatively, the target substance may be collected after the elution from the Component.

As a non-limiting example, the blood donor plasma treatment may then be used with a view to providing a plasma which for example is free from, or has a reduced amount of, for example blood group specific antibodies (if the Component contains blood group antigen). Alternatively, as a non-limiting example, antibodies or proteins may be eluted from the Component after the treatment and may be collected.

Non-limiting examples of the Component have been disclosed above. As mentioned above, the Component may contain, as a non-limiting example, a covalently bound saccharide, an antibody, or another protein, but may also, as a non-limiting example, contain a covalently bound positively or negatively charged molecule, e.g. a molecule containing an amine or a carboxyl group, a hydrophobic organic molecule, e.g. an alifatic or aromatic organic molecule, or e.g. a receptor substance, an amino acid, e.g. tryptophan or a monomeric, oligomeric, or polymeric derivative thereof, or a peptid or a monomeric, oligomeric, or polymeric derivative thereof.

The Component may also consist of a polymer which has been produced in a polymerisation of monomers in the presence of the target substance which is to be refined or isolated, e.g. a drug substance or an environmental toxin, or a degradation product. After washing the produced polymer, this is washed free from the target substance. The resulting so-called imprinted polymer may according to the present invention then be used for isolating of the target substance or refining of the target substance from the treated liquid. According to the invention a coarse filtration of the liquid is made in such a way in step 1.

Non-limiting examples of a saccharide which may be covalently bound to the matrix in the component are mono-, di-, tri-, tetra-, penta- or higher oligosaccharides or oligosaccharide derivatives, which may be monomeric, dimeric or oligomeric derivatives of the saccharide. Examples of monosaccharide units which may be present in the saccharide are one or more of D-galactose, D-mannose, D-glucose, N-acetyl-D-galactosamine, L-fucose, N-acetyl-D-glucosamine, N-acetylneuramic acid, below abbreviated as Gal, Man, Glc, GalNAc, Fuc, GlcNAc, and Sia, respectively.

Non-limiting examples are saccharides containing one of or a combination of at least two of the blood group sequences for blood group A, for example
GalNAcα1-3(Fucα1-2)Galβ1-,
GalNAcα1-3(Fucα1-2)Galβ1-3GalNAcβ

GalNAcα1-3(Fucα1-2)Galβ1-3GlcNAc
GalNAcα1-3(Fucα1-2)Galβ1-4GlcNAc

Other non-limiting examples are saccharides containing any one or a combination of at least two of the blood group sequences for blood group B, for example
Galα1-3(Fucα1-2)Galβ1-,
Galα1-3(Fucα1-2)Galβ1-3GalNAcβ
Galα1-3(Fucα1-2)Galβ1-3GlcNAc
Galα1-3(Fucα1-2)Galβ1-4GlcNAc Other non-limiting examples are saccharides containing any one or a combination of at least two of the blood group sequences for blood group H, for example
Fucα1-2Galβ1-,
Fucα1-2Galβ1-3GalNAcβ
Fucα1-2Galβ1-3GlcNAc
Fucα1-2Galβ1-4GlcNAc The saccharide may be present in the form of a monomeric or oligomeric derivative bound via an aglycon to the matrix forming the Component. A non-limiting example thereof is the blood group A derivative GalNAcα1-3(Fucα1-2)Galβ1-O—(CH$_2$)$_2$PhNH covalently bound to a carbonyl group (C=O) on the matrix forming an amide bond. The amide bond may be obtained via a so-called EDC/NHS reaction, in which a carboxylic group on the matrix is activated and thereafter is brought to react with the saccharide derivative, constituting a non-limiting example of the Component.

In the same way an antibody or another protein, for example, may be bound to the matrix.

The matrix may for example consist of cross-linked or non-cross-linked agarose. This form of the matrix is commercially available for example as the trade name Sepharose in different variants in view of cross-linking and concentration, e.g. Sepharose 4FF, 2B, 4B or CL 2B, CL 4B or 6B.

Other non-limiting examples of saccharides are lactosamine, Galβ1-4GlcNAcβ1-3Galβ1-4GlcNAc, saccharides containing GlcNAc, against which anti-GlcNAc specific antibodies are formed, blood group P$_1$, blood group P$^k$, Lewis blood group substances, gangliosides, such as GM$_1$, GM$_2$, Gd$_1$, Gd$_2$, other sialylated saccharides, sulfated saccharides and glucoronic acid-containing saccharides.

The treatment according to the present invention with the Component containing blood group A and/or B saccharide (s) may be used for the treatment of a patient before or in connection with a so-called blood group compatible transplantation, e.g. in transplantation of organs or stem cells from donors belonging to blood group A, AB or B to recipients belonging to blood group 0, with a view to specifically eliminating/reducing anti-A; Anti-A and anti-B; and anti-B antibodies, respectively, binding to the A and B saccharide, respectively, in the Component.

The treatment can also be used with a view to extracting the above-mentioned anti-A and/or anti-B antibodies from blood donor plasma or with a view to producing a blood donor plasma without said anti-A and/or anti-B antibodies, or in a reduced amount.

Antibodies from blood donor plasma is today extracted for therapeutic purposes, such as intravenous immunoglobuline (IVIG). The present invention may be used for the production of IVIG having a reduced amount of anti-A and/or anti-B antibodies, wherein IVIG, or during the production of IVIG blood donor plasma or protein or the antibody fraction, is treated by use of the method according to the present invention and the component containing A- and/or B-saccharide.

Antibodies active against pathogenic bacteria or viruses may for example also be extracted from for example blood donor plasma by use of a method according to the present invention. In connection therewith, the component containing for example any one of the blood group determinants A, B, GlcNAc-containing saccharide or any other saccharide can be used.

Antibodies against Galα1-3Gal saccharides may be extracted in the same way from for example blood donor plasma according to the present invention with the Component containing a Galα1-3Gal saccharide sequence.

In the same way treatments for other applications, e.g. certain autoimmune diseases, e.g. Guillain-Barré syndrome, myasthenia gravis, may be performed according to the present invention, wherein the Component contains other of the saccharides exemplified above. The saccharides in the Component are chosen by the person skilled in the art and do not limit the scope of the present invention.

In connection with certain autoimmune diseases, for example protein A or antibody, or other types of protein, amino acid, or peptide containing columns for reduction of antibodies/proteins are used.

The present invention refers to an alternative treatment according to steps 1 and 2 in the FIGURE above, with a Component containing protein A or antibody, or other types of protein, amino acid, or peptide bound to the matrix.

The exact conditions in each application of the present invention is chosen by the person skilled in the art for the specific case, e.g. the size of filter 1 and 2, the initiation/start of the treatment, the flow—treated volume/min, temperature, treatment period, amount of component per treatment. A different amount of the component may be chosen, for example, in the treatment of different patients depending on the patient's size and antibody titres (titer of e.g. anti-A/ anti-B antibodies). The amount of the component per patient treatment may e.g. be from 1 ml and up to 100 ml, or any amount therebetween. The time period may e.g. be from 10 minutes up to e.g. 4 hours or any time period therebetween, which is decided from case to case by the person skilled in the art.

Anti-coagulation liquid in the treatment of for example a patient or blood, the flow rates and other treatment parameters may be chosen by the person skilled in the art to be similar/corresponding to those used in DFPP. One of the differences is, as mentioned above, that the patient regains his plasma substantially intact by use of the present invention, in contrast to the previous accessible treatment, PE or DFPP.

The Component may be delivered to the user in sterile form. The Component may be present, for example, in a sterile packaged form. The sterilization of the Component may be performed, for example, in connection with for example a GMP production, by autoclavation of saccharide-containing Components.

The invention claimed is:

1. A method for blood treatment or purification, comprising
separating blood cells from plasma in a first filter or a first centrifuge,
transporting the separated plasma onwards in a plasma conduit and mixing the separated plasma with a suspension containing at least one component specifically binding a target substance that is to be reduced in the blood such that the mixture of the component and separated plasma is transported together toward a second filter or a second centrifuge,
separating both the component and the component having the target substance bound thereto from the plasma in the second filter or the second centrifuge, wherein the plasma having a reduced content of target substance passes through pores of the second filter or a separating element of the second centrifuge, the separated component and/or the separated component having the target substance bound thereto
   a) are returned to the plasma,
   b) are transported to a waste bag, or
   c) are collected for refining the target substance from the component by elution, the component comprises a non-soluble polymer matrix and at least one covalently bound ligand, the target substance is an antibody, a protein, a virus, bacteria, or a cell, and recirculating the plasma having a reduced content of the target substance to the blood cells, wherein purified blood is obtained.

2. The method according to claim 1, wherein the target substance is a blood group specific antibody.

3. The method according to claim 2, wherein the blood group specific antibody is an anti-A, an anti-A and anti-B, or an anti-B antibody.

4. The method according to claim 1, wherein the target substance is an antibody active against pathogenic bacteria or viruses.

5. The method according to claim 1, wherein the ligand is a saccharide, a protein or an antibody.

6. The method according to claim 5, wherein the saccharide is a mono-, di-, tri-, tetra-, penta- or higher oligosaccharide or a oligosaccharide derivative.

7. The method according to claim 5, wherein the saccharide contains one of or a combination of at least two of the blood group sequences for blood group A, one of or a combination of at least two of the blood group sequences for blood group B, or one of or a combination of at least two of the blood group sequences for blood group H.

8. The method according to claim 1, wherein the ligand is provided with a spacer distancing the matrix from the ligand.

9. The method according to claim 1, wherein the component is added continuously.

10. A method for therapeutic treatment or purification of a patient's blood, wherein blood is extracted from the patient, the blood is treated by the method according to claim 1, and the purified blood obtained is returned to the patient.

11. The method according to claim 2, wherein the component is added continuously.

12. The method according to claim 4, wherein the component is added continuously.

13. The method according to claim 6, wherein the component is added continuously.

14. The method according to claim 1, wherein the non-soluble polymer matrix is a plastic or a polysaccharide.

15. The method according to claim 14, wherein the polysaccharide is a cross-linked agarose.

16. The method according to claim 10, wherein the non-soluble polymer matrix is a plastic or a polysaccharide.

17. The method of claim 1, wherein the second filter and the second centrifuge each have an internal upstream feed region and a downstream filtrate region, and the plasma having the reduced content of target substance passes from the upstream feed region to the downstream filtrate region.

18. The method of claim 17, wherein the second filter and the second centrifuge each have a downstream pass through region that allows passage of the component and the component having the target substance bound thereto.

19. The method of claim 1, wherein the non-soluble polymer matrix is about 1 μm to about 300 μm in particle size.

20. A method for blood treatment or purification, comprising
   separating blood cells from plasma in a first filter or a first centrifuge,
   transporting the separated plasma onwards in a plasma conduit and mixing the separated plasma with a suspension containing at least one component specifically binding a target substance that is to be reduced in the blood such that the mixture of the component and separated plasma is transported together toward a second filter downstream of the first filter or first centrifuge,
   separating both the component and the component having the target substance bound thereto from the plasma in the second filter downstream of the first filter or first centrifuge, wherein the second filter is porous and the plasma having a reduced content of target substance passes through pores of the second filter,
   the separated component, and/or the separated component having the target substance bound thereto
      a) are returned to the plasma,
      b) are transported to a waste bag, or
      c) are collected for refining the target substance from the component by elution,
   the component comprises a non-soluble polymer matrix and at least one covalently bound ligand,
   the target substance is an antibody, a protein, a virus, bacteria, or a cell, and
   recirculating the plasma having the reduced content of the target substance to the blood cells, wherein purified blood is obtained.

21. The method of claim 20, wherein the second filter has a pore size that is sized as to allow for complete passage of the plasma having the reduced content of target substance.

22. A method for blood treatment or purification, comprising
   separating blood cells from plasma in a first filter or a first centrifuge,
   transporting the separated plasma onwards in a plasma conduit and mixing the separated plasma with a suspension containing at least one component specifically binding a target substance that is to be reduced in the blood such that the mixture of the component and separated plasma is transported together toward a second filter downstream of the first filter or first centrifuge,
   separating both the component and the component having the target substance bound thereto from the plasma in the second filter downstream of the first filter or first centrifuge, wherein the second filter is porous and the component and the component having the target substance bound thereto do not pass through pores of the second filter,
   the separated component and/or the separated component having the target substance bound thereto
      a) are returned to the plasma,
      b) are transported to a waste bag, or
      c) are collected for refining the target substance from the component by elution,
   the component comprises a non-soluble polymer matrix and at least one covalently bound ligand,
   the target substance is an antibody, a protein, a virus, bacteria, or a cell, and recirculating the plasma having the reduced content of the target substance to the blood cells, wherein purified blood is obtained.

23. The method of claim 1, wherein the component and the component having the target substance bound thereto, after leaving the second filter or the second centrifuge, are separated and the component without the target substance bound thereto is recirculated for mixing with the separated plasma from the first filter or first centrifuge.

24. The method of claim 1, wherein the first and second filters are utilized and the first filter is a coarser filter than the second filter.

* * * * *